United States Patent [19]

Marijnissen et al.

[11] Patent Number: 4,848,323
[45] Date of Patent: Jul. 18, 1989

[54] APPARATUS FOR, AND METHOD OF, EXAMINING AND/OR ILLUMINATING A BODY CAVITY

[75] Inventors: Johannes P. A. Marijnissen, Oud Beijerland; Harald Jansen, Schipluiden; Willem M. Star, Mijnsheerenland, all of Netherlands

[73] Assignee: Daniel Den Hoed Stichting, Rotterdam, Netherlands

[21] Appl. No.: 154,976

[22] Filed: Feb. 9, 1988

[30] Foreign Application Priority Data

Feb. 11, 1987 [NL] Netherlands ................. 8700329

[51] Int. Cl.$^4$ .............................................. A61B 1/00
[52] U.S. Cl. ....................................................... 128/6
[58] Field of Search ..................... 128/3, 4, 5, 6, 7

[56] References Cited

U.S. PATENT DOCUMENTS

| | | | |
|---|---|---|---|
| 4,198,960 | 4/1980 | Utsugi | 128/6 |
| 4,250,873 | 2/1981 | Bonnet | 128/7 |
| 4,619,247 | 10/1986 | Inoue et al. | 128/6 |
| 4,718,419 | 1/1988 | Okada | 128/4 X |

FOREIGN PATENT DOCUMENTS

| | | |
|---|---|---|
| 189329 | 7/1986 | European Pat. Off. . |
| 3323365 | 3/1984 | Fed. Rep. of Germany . |

OTHER PUBLICATIONS

The Journal of Urology, vol. 131, May 1984, pp. 884–887.
The Journal of Urology, vol. 133, Feb. 1985, pp. 311–315.
The Journal of Urology, vol. 134, Oct. 1985, pp. 678.
CRC Critical Reviews in Oncology/Aematology, vol. 2, No. 2.1–1984, pp. 83–115.

Primary Examiner—William H. Grieb
Attorney, Agent, or Firm—Cooper & Dunham

[57] ABSTRACT

Apparatus for examining a cavity in a body, comprising a cannula with accessories which via the cannula can be disposed to extend into such cavity. At least one accessory is arranged to receive one or more conductors. The accessory arranged to receive conductors comprises a relatively stiff mandrin disposed for movement between a plurality of substantially parallel capillaries. Each capillary contains at least adjacent its end, a tubular body of translucent material, the ends of said tubular bodies remote from the respective capillaries being connected to each other and to the end of the mandrin. The apparatus is arranged to receive at least one further accessory for introducing a light source into the cavity. In use the cannula is disposed so that at least one end extends into the cavity, the accessory with mandrin and capillary are introduced into the cannula, the mandrin with the tubular bodies are moved in the cavity until the end rests against the wall of the cavity, the tubular bodies are moved further for them to come to rest against the wall of the cavity. A photodetector attached to the end of a fiber-type photoconductor is introduced through each of the capillaries into each of the tubular bodies so that they are each positioned at a corresponding position in the middle of the tube. A light source is introduced through the cannula into the cavity until the different light detectors each measure virtually the same amount of light.

9 Claims, 3 Drawing Sheets

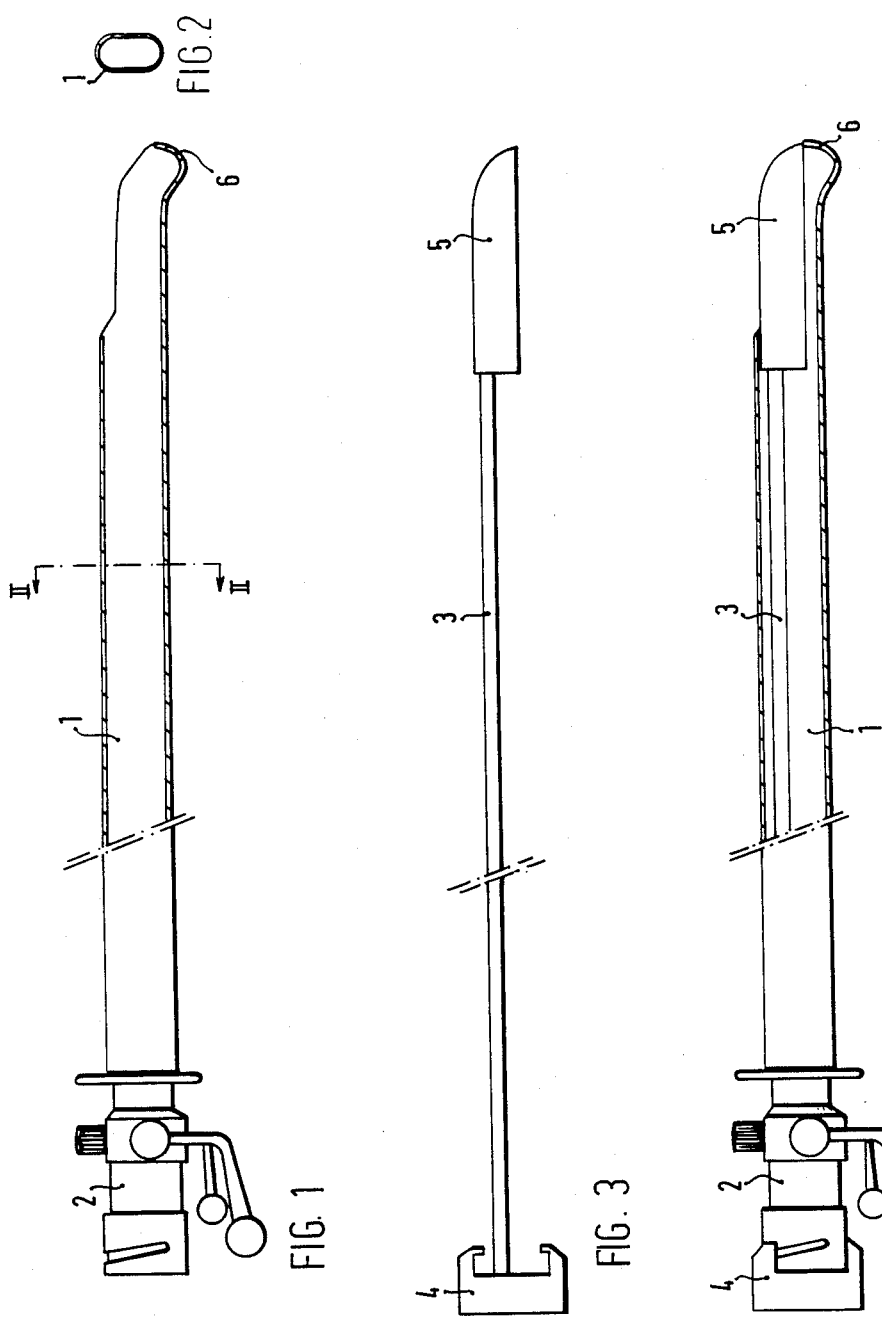

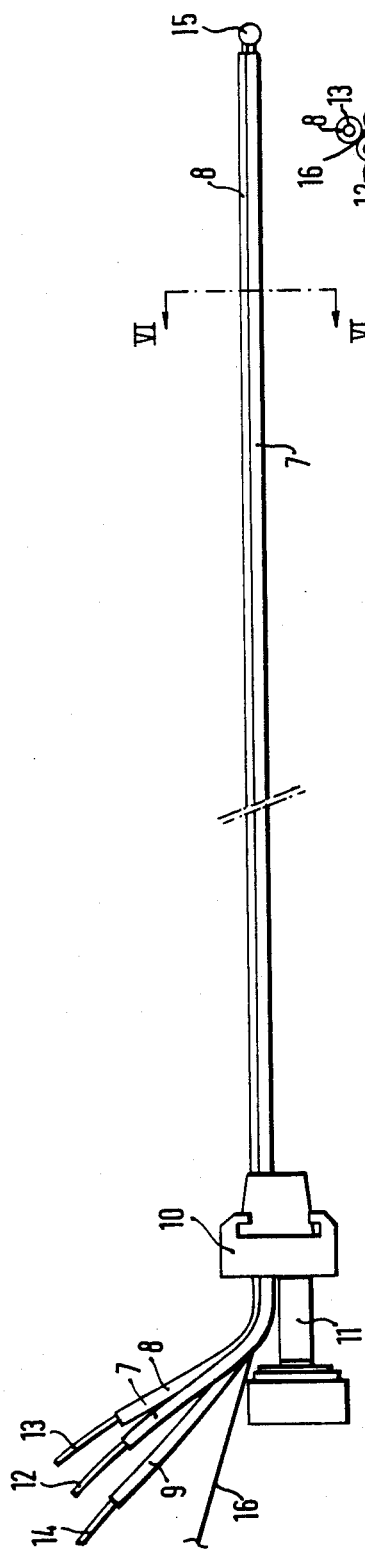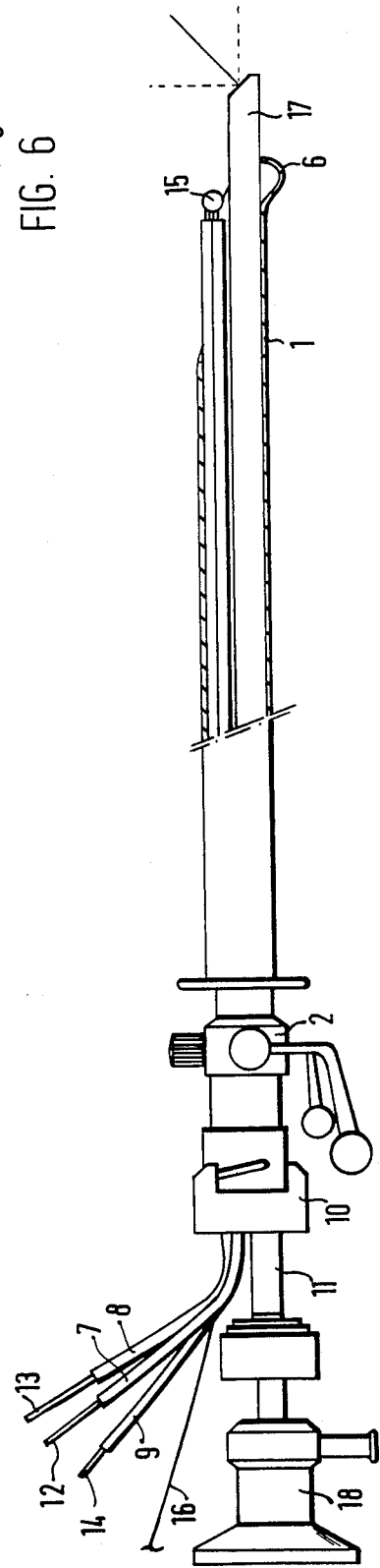

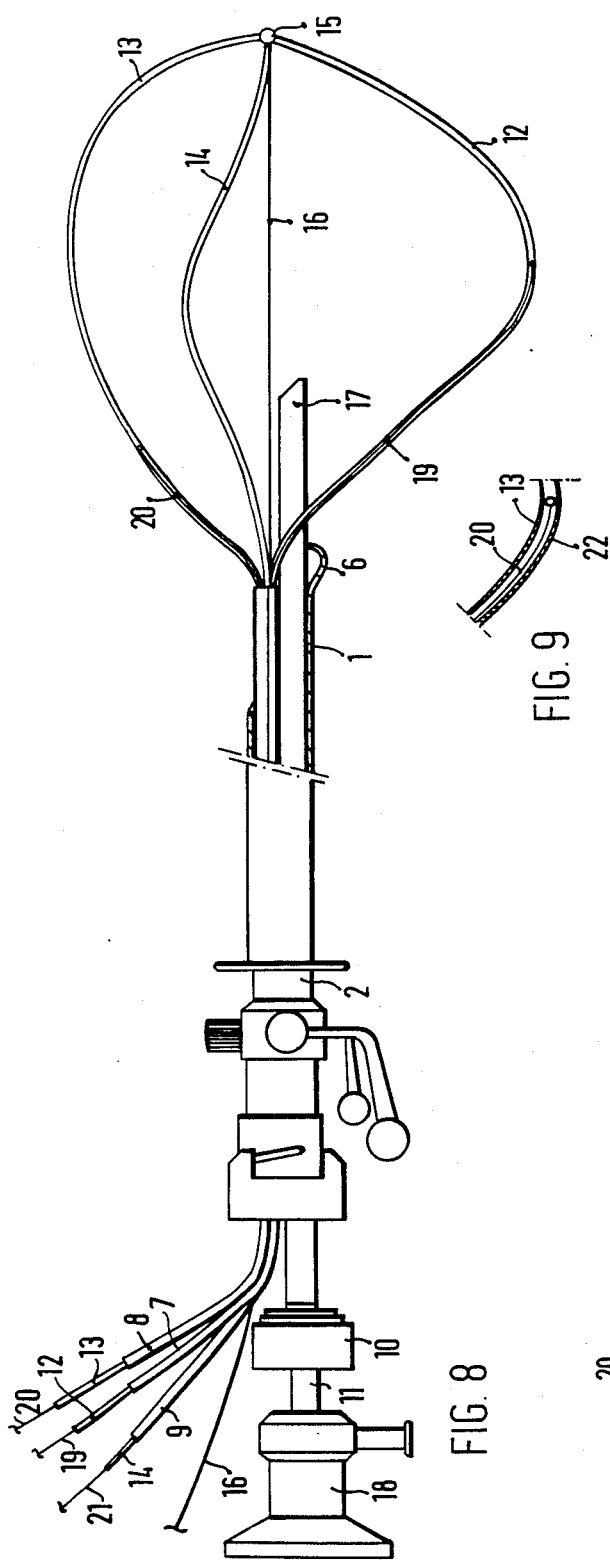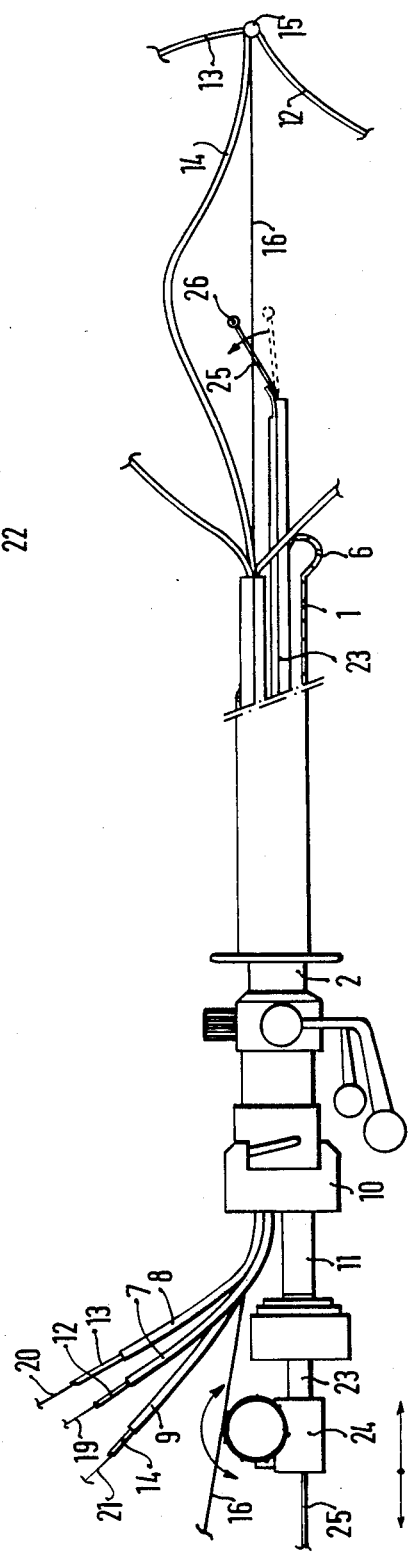
FIG. 8  FIG. 9  FIG. 10

APPARATUS FOR, AND METHOD OF, EXAMINING AND/OR ILLUMINATING A BODY CAVITY

This invention relates to apparatus for examining and/or illuminating a cavity in a body, comprising a cannula with accessories which via the cannula can be disposed to extend into such cavity to be examined and/or to be illuminated, there being at least one accessory arranged to receive one or more conductors. The invention further relates to a method of examining and/or illuminating a cavity in a body, using the apparatus, in which the cannula of the apparatus is disposed so that one end extends into the cavity.

An apparatus and method of the above kinds are disclosed in German Offenlegungsschrift No. 3,323,365. One possible application of the prior apparatus and method is to introduce the apparatus into the bladder of a human being or animal and internally illuminating the bladder for combatting malign or pre-malign conditions. Such a photodynamic therapy is described and elucidated in more detail in articles in the Journal of Urology, Volume 131 (1984) pp 884-887; Volume 133 (1985) pp 311-315; Volume 134 (1985) pp 675-678 and in CRC Critical Reviews in Oncology/Hematology, Volume 2, Issue 2 (1984) pp 83-116, among other articles. In this method it is desirable that the entire wall of the bladder is uniformly illuminated. Generally speaking, it is often desirable in examining and/or illuminating a cavity that the illumination should be uniform. For this purpose the light source should be disposed in a suitable location.

In the method disclosed in the above Offenlegungsschrift, a light-scattering liquid is introduced into the cavity (the bladder) in the illuminating mode. As a result of the presence of this fluid, the light is scattered many times before reaching the bladder wall. As a consequence, the illumination of the wall becomes diffuse. According to the Offenlegungsschrift, the light intensity at the wall would be less dependent on the distance from the light source than would be the case without a scattering fluid. Also, a substantially uniform illumination of the entire wall is claimed to be possible.

One disadvantage of the prior method and apparatus is that these are limited to applications using a light-scattering fluid. When a clear fluid is used, a uniform illumination is not possible without more ado, and even when a light-scattering fluid is used, such an illumination cannot be accomplished under all conditions. There was accordingly a need for an apparatus and a method enabling the light source to be better positioned, and enabling observations with regard to the illumination to be made both during positioning and, if desired, during illumination.

It is an object of the present invention to provide a method and an apparatus in which the disadvantages of the prior method and apparatus, as outlined above, do not occur, or at any rate to a much lesser extent.

The object contemplated is achieved, in accordance with the present invention, with an apparatus in which the accessory arranged to receive conductors comprises a relatively stiff mandrin disposed for movement between a plurality of substantially parallel capillaries, each capillary containing, at least adjacent its end, a tubular body of translucent material, the ends of said tubular bodies remote from the respective capillaries being connected to each other and to the end of the mandrin, the apparatus optionally being arranged to receive, in addition to said accessory, at least one further accessory for introducing a light source into the cavity to be examined or illuminated; and with a method comprising introducing the accessory with mandrin and capillary into the cannula, moving the mandrin with the tubular bodies in the cavity until the end rests against the wall of the cavity, moving the tubular bodies, which as far as necessary are pre-shaped, further for them to come to rest against the wall of the cavity throughout their length outside the cannula and at suitable angles to each other, introducing a photodetector attached to the end of a fiber-type photoconductor through each of the capillaries into each of the tubular bodies so that they are each positioned at a corresponding position virtually in the middle of the tube, and further introducing a light source through the cannula into the cavity, and moving said light source until the different light detectors each measure virtually the same amount of light, and then fixing the light source in that position.

By means of the apparatus and the method according to the invention, it is possible not only to measure the light intensity at different critical positions on the bladder wall during the positioning of the light source, so that ultimately the optimum location of the light source can be determined, but also, during the illumination the light intensity can be checked, if desired continuously. This is useful especially during illumination as a part of a photodynamic therapy to prevent damage from underdosage or overdosage and to indicate the dosage of light with reasonable accuracy, so that the correlation between dose and effect can be recorded.

The apparatus according to the invention is also applicable for examining the amount of radiation received in the wall of a cavity, for example in case parts located next to, or adjacent to the cavity are irradiated. In such an application, no light detectors coupled with photoconductors are disposed in the tubes of the apparatus according to the invention, but instead detectors for ionizing radiation, coupled to suitable conductors.

The tubular bodies disposed in at least a portion of the respective capillaries of the accessory of the apparatus according to the invention can suitably be tubules of a slightly deformable synthetic plastics material. Such tubules, for example of nylon, are very suitable for being pre-formed. In one suitable embodiment, the method according to the invention comprises first measuring the length of the cavity by moving the mandrin up to the wall of the cavity, removing the mandrin and capillaries with tubular bodies from the apparatus, pre-forming the tubular bodies using surroundings of elevated temperature, temporarily straightening the tubular bodies again, and re-introducing the mandrin with capillaries and tubular bodies into the apparatus. The pre-forming treatment can be effected, for example, by means of hot water.

In the apparatus according to the invention, said at least one other accessory may be a tubular element with a fiber-optic photoconductor mounted for movement therein and arranged to be moved outside the tubular element. Preferably, the fiber-optic photoconductor carries a light-diffusing bulb at the end to be moved outside the tubular element. The fiber-optic photoconductor is then arranged to be connected at its other end to a light source, for example, a laser. In this way the bulb becomes an isotropic light source which, provided arranged in the correct manner, uniformly illuminates the wall of the cavity, which may be filled with a clear liquid, for example, physiological saline.

In the apparatus according to the invention, the accessory arranged to receive photoconductors preferably comprises three capillaries and three tubules disposed within said capillaries. In operation, the ends of the three tubules are deployed at an angle of about 120° relatively to each other until they rest like whalebones against the wall of the cavity. Detectors secured to fiber-optic photoconductors are moved through the capillaries up to the ends of the tubes. The photoconductors are coupled to suitable electronic processing equipment to provide for a continuous reading of the light intensity received by the detectors. By moving the light source the same intensity for each of the detectors can be aimed at. At the moment when that is reached, the light source has its optimum position. Naturally, it is also possible for the apparatus according to the invention to be designed with more than three capillaries and tubules. This, however, does not produce any appreciable better results, and does increase the size of the equipment.

In a suitable embodiment, the tubules of the apparatus according to the invention can be provided with a bar marking, and if desired, the detector fibers can also be provided with bar markings. In this way an accurate location of the detectors in the tubes can be realized.

The apparatus according to the invention can be used, for example, to combat malign or pre-malign conditions in the wall of the human or animal bladder. This includes administering to the patient a photosensitive substance, which substance is preferentially absorbed by malign or pre-malign tissue. In this way, the substance accumulates in malign or pre-malign superficial growths in the wall of the bladder. The apparatus according to the invention is introduced as usual for cystoscopes, and the light source is positioned in the correct position with a laser source operated at a low intensity. Thereafter the treatment proper is effected by increasing the intensity. This treatment can be continuously monitored and controlled by means of the light detectors in the tubules of the one accessory, connected to the electronic signal processing apparatus.

The apparatus according to the invention can also be used in examining cavities which are not by themselves able to retain a liquid. In such cases, a balloon may be secured at the end of the apparatus over the top of the cannula, so that, in operation, the system of tubules is deployed into the balloon and the balloon thus forms an intermediate wall between the cavity wall and the system of tubules. It is noted in this connection that the use of a balloon is known per se from the above German Offenlegungsschrift No. 3,323,365.

The invention is illustrated with reference to the accompanying drawings, in which:

FIG. 1 shows the cannula of one embodiment of the apparatus according to the invention;

FIG. 2 shows a cross-sectional view, taken on the line II—II of the cannula shown in FIG. 1;

FIG. 3 shows a mandrin for use in introducing the cannula shown in FIG. 1;

FIG. 4 illustrates the assembly of cannula and mandrin;

FIG. 5 shows an accessory with light detection means of the apparatus according to the invention;

FIG. 6 shows a cross-sectional view of the accessory illustrated in FIG. 5, taken on the line VI—VI thereof;

FIG. 7 shows an assembly of cannula, accessory and additional optics;

FIG. 8 shows the assembly of FIG. 7 with deployed light detectors;

FIG. 9 shows a detail of the light detection system; and

FIG. 10 the embodiment as in use in operation.

FIG. 1 shows a side-elevational view of the cannula of one embodiment of the apparatus according to the invention. The cannula is in essence a conventional cystoscopic cannula of oval cross-sectional configuration. The hollow cannula tube is provided at one end with the conventional operating handle 2. FIG. 2 is a cross-sectional view of cannula 1, taken on the line II—II. FIG. 3 shows a conventional mandrin 3, which in essence consists of a rod with a handle 4 at one end and a hood-shaped element 5 at the other. FIG. 4 illustrates how mandrin 3 and cannula 1 can be combined into one unit, with the hood 5 of mandrin 3 closing the more or less spoon-shaped open end 6 of the cannula. In the form illustrated in FIG. 4, the apparatus according to the invention can be introduced, for example, with the tip into the bladder cervix of a patient. After the introduction of the cannula, the mandrin is removed, and the accessory illustrated in FIG. 5 is positioned in the canal of the cannula 1.

The accessory illustrated in FIG. 5 comprises three essential parallel capillaries 7, 8 and 9, for example of stainless steel, attached to a suitable operating handle 10, so that, in the hollow handle 10, through which the capillaries extend to outside the handle, the capillaries leave a passage to which a supply tube 11 is connected. Through supply tube 11, further accessories can be introduced into cannula 1 in more or less fixed position relative to capillaries 7, 8 and 9, as will be described more fully hereinafter. A cross-sectional view of the system of capillaries, taken on the line VI—VI of FIG. 5, is illustrated in FIG. 6. Disposed in the capillaries are nylon tubules, i.e. tubules 12, 13 and 14 in the respective capillaries 7, 8 and 9. Tubules 12, 13 and 14 are transparent and, for example, have a diameter of less than 1.2 mm. At their end, the tubules are secured to a hinge system 15. Hinge system 15 is further secured to the end of a more or less stiff, filamentous mandrin 16, disposed for movement between capillaries 7, 8 and 9. By moving mandrin 16 forwardly, tubules 12, 13 and 14 are moved with the hinge system 15 relatively to the capillaries and are also pushed forwardly.

FIG. 7 illustrates how the accessory of FIG. 5 is positioned in the cannula 1 of FIG. 1, while at the same time another accessory, essentially consisting of known cystoscope-optics, including a tubular body 17 and a handle with eyepiece 18, is disposed in cannula 1. Through the cystoscope-optics, the operator can observe what happens in the cavity into which the tip of the cannula 1 extends. The operation of the unit has assembled is shown in more detail in FIG. 8. When the unit of FIG. 7 has been introduced into, for example, the bladder cervix of a patient, the mandrin 16 is operated to move the hinge system 15 with the tubules 12, 13 and 14 coupled to it forwardly relatively to cannula 1 until the hinge system 15 rests against the bladder wall. All this is realized by monitoring through the cystoscope-optics. The tubules 12, 13 and 14, which are preformed, bulge outwardly as soon as they are moved inside the capillaries 7, 8 and 9 and are pushed up and guided against the bladder wall one by one. The tubules 12, 13 and 14 accordingly follow the shape of the bladder wall, as shown diagrammatically in FIG. 8. The correct disposition of the tubules 12, 13 and 14 can be monitored by means of the cystoscope-optics, as the coupling through handle 18 and seals between optics and cannula 1 have been arranged so that the optics can rotate and move in an out independently of the cannula. When the tubules 12, 13 and 14 have been disposed at the correct spaced interrelationship, which means that they will enclose angles of about 120° with each other, the cannula 1 is fixed, because cannula 1 with mandrin 16 and capillaries 7, 8 and 9 constitute the support points for tubules 12, 13 and 14.

After tubules 12, 13 and 14 have been positioned, the optics can be removed. Furthermore, light detectors connected to fiber-optic photoconductors can be introduced into tubules 12, 13 and 14, so that these detectors are disposed approximately halfway the convex part of the respective tubules. FIG. 8 shows the fiber-optic photoconductors 19, 20 and 21, respectively guided in tubules 12, 13 and 14. FIG. 9 shows in detail how the isotropic fiber-detector 22 is disposed at the end of the fiber-optic photoconductor 20, and the whole is located within tubule 13, so that the detector is capable of measuring the light intensity of the bladder wall in situ through the thin transparent wall of tubule 13 (which has a thickness of less than about 0.1 mm).

FIG. 10 illustrates how, in the illuminating phase, the cystoscope-optics (17, 18 in FIG. 8) has been removed and replaced by an accessory by means of which the light source is introduced. This accessory is in essence a thin hollow tube 23 with an operating handle 24. Passed through tube 23 of the accessory is a fiber-optic photoconductor 25 which outside the apparatus is coupled to a light source not shown, for example, a laser system. Mounted on the tip of the photoconductor 25 to be introduced into the cavity is a light-scattering bulb 26, which in operation serves as the light source for illuminating the wall of the cavity into which the end of the apparatus extends when installed in position. The accessory with the photoconductor 25 is arranged to rotate and slide relatively to cannula 1 independently thereof, while further the accessory may be provided with means for causing the end of photoconductor 25 with bulb 26 to deflect or bend somewhat. FIG. 10 shows such bending diagrammatically with an end in solid lines and an end in dotted lines. In this way sufficient freedom of movement is provided for the light source constituted by bulb 26 for it to be accurately disposed in the "optical center" of the cavity, guided by the observations by means of the detectors within tubules 12, 13 and 14.

In operation, as stated before, the fiber-optic photoconductor 25 is coupled to a light source, such as a laser system. The fiber-optic photoconductors 19, 20 and 21 of the detection system are coupled to photodiodes for light-to-current conversion. Reading is effected by conventional apparatus, analogue and/or digital. In illumination for therapeutic purposes, it is of importance that the integrated light dose should be measured, too. This comprises measures well-known to those skilled in the art, which need not be described in any detail herein.

What we claimed is:

1. Apparatus for examining and/or illuminating a cavity in a body, comprising a cannula with accessories which via the cannula can be disposed to extend into such cavity to be examined and/or to be illuminated, there being at least one accessory arranged to receive one or more conductors, characterized in that the accessory arranged to receive conductors comprises a relatively stiff mandrin disposed for movement between a plurality of substantially parallel capillaries, each capillary containing, at least adjacent its end, a tubular body of translucent material, the ends of said tubular bodies remote from the respective capillaries being connected to each other and to the end of the mandrin, the apparatus being arranged to receive, in addition to said accessory, at least one further accessory for introducing a light source into the cavity to be examined or illuminated.

2. Apparatus as claimed in claim 1, characterized in that the tubular bodies are tubules of a slightly deformable synthetic plastics material.

3. Apparatus as claimed in claim 1 characterized in that said at least one other accessory is a tubular element with a fiber-optic photoconductor mounted for movement therein and arranged to be moved outside the tubular element.

4. Apparatus as claimed in claim 3, characterized in that the fiber-optic photoconductor carries a light-diffusing bulb at the end to be moved outside the tubular element.

5. Apparatus as claimed in claim 3 characterized in that the accessory arranged to receive photoconductors comprises three capillaries and three tubules disposed within said capillaries.

6. Apparatus as claimed in claim 1 characterized in that a balloon is attached to the end of the apparatus to surround the tip of the cannula.

7. A method of examining and/or illuminating a cavity in a body using the apparatus as claimed in claim 1 in which the cannula of the apparatus is disposed so that at least one end extends into the cavity, characterized by the steps of introducing the accessory with mandrin and capillary into the cannula, moving the mandrin with the tubular bodies in the cavity until the end rests against the wall of the cavity, moving the tubular bodies, which as far as necessary are pre-shaped, further for them to come to rest against the wall of the cavity throughout their length outside the cannula and at suitable angles to each other, introducing a photodetector attached to the end of a fiber-type photoconductor through each of the capillaries into each of the tubular bodies so that they are each positioned at a corresponding position virtually in the middle of the tube, and further introducing a light source through the cannula into the cavity, and moving said light source until the different light detectors each measure virtually the same amount of light, and then fixing the light source in that position.

8. A method as claimed in claim 7, characterized by the steps of first measuring the length of the cavity by moving the mandrin up to the wall of the cavity, removing the mandrin and capillaries with tubular bodies from the apparatus, pre-forming the tubular bodies using surroundings of elevated temperature, temporarily straightening the tubular bodies again, and re-introducing the mandrin with capillaries and tubular bodies into the apparatus.

9. Apparatus as claimed in claim 2 characterized in that said at least one other accessory is a tubular element for a fiber-optic photoconductor mounted for movement therein and arranged to be moved outside the tubular element.

* * * * *